United States Patent
Singh et al.

(10) Patent No.: US 6,924,127 B2
(45) Date of Patent: Aug. 2, 2005

(54) SPECIES SPECIFIC DNA SEQUENCES AND THEIR UTILIZATION IN IDENTIFICATION OF VIOLA SPECIES AND AUTHENTICATION OF "BANAFSHA" BY POLYMERASE CHAIN REACTION

(75) Inventors: Mahipal Singh, Palampur (IN); Chandan Sharma, Palampur (IN); Brij Lal, Palampur (IN)

(73) Assignee: Council of Scientific & Industrial Research, New Delhi (IN)

( * ) Notice: Subject to any disclaimer, the term of this patent is extended or adjusted under 35 U.S.C. 154(b) by 281 days.

(21) Appl. No.: 10/232,566

(22) Filed: Sep. 3, 2002

(65) Prior Publication Data

US 2003/0119032 A1 Jun. 26, 2003

Related U.S. Application Data

(62) Division of application No. 09/698,283, filed on Oct. 30, 2000, now Pat. No. 6,465,637.

(51) Int. Cl.$^7$ ............................................. C12P 19/34
(52) U.S. Cl. ......................................... 435/91.2; 435/6
(58) Field of Search ................................... 435/91.2, 6

(56) References Cited

U.S. PATENT DOCUMENTS 6,569,625 B1 * 5/2003 Tsim et al. ..................... 435/6

OTHER PUBLICATIONS

GenScript Corporation Online Catalog. www.genscript.com, downloaded Aug. 5, 2004.*
Singh et al. (Biochimica et Biophysica Acta 1444(1999) 263–268).*
Amersham Life Science (1994) Catalog, p. 72–73).*
Kolchinsky et al. (Genome (1991) vol. 34, p. 1028–1031).*
Sandaa et al. (FEMS Microbiology Ecology, 30 (1999) 237–251).
Berger (South African Journal of Botany, 2004, 70(1):173–180).
Wealth of India, PID, CSIR, New Delhi, vol. X, 1976, pp. 514–517.
Yan–Bo Zhang et al., Random Primed Polymerase Chain Reaction Differentiates Codonopsis Pilosula From Different Localities, Planta Medica, Georg Theme Verlag Stuttgatt, vol. 65, 1999, pp. 157–160.
H.L. Ko et al., "Identification of Cereals Using the Polymerase Chain Reaction", J. of Cereal Science, Academic Press Limited, vol. 19, 1994, pp. 101–106.
K. Kheterpal et al., "Study of a Unani, Polypharmaceutical Preparation Joshina as Antitussive and Experimental Models," Indian J. of Pharmacology, vol. 19, 1987, pp. 200–204.
H.J. On et al., "Identification of the Series–Specific Random Amplified Polymorphic DNA Markers of Viola Species," Plant Breeding, Blackwell Wissenschafts–Verlag, vol. 117, 1998, pp. 295–296.
K.L. Handa et al., "The Present Position of the Crude Drugs Used in the Indigenous Medicine", Indian J. of Pharm., 1951, pp. 29–43.
ZH Cai et al., "Molecular Diversity of 5S–rRNA Spacer Domain in Fritillaria Species Revealed by PCR Analysis," Planta Medica, Georg Theme Verlag Stuttgatt, 1999, pp. 360–364.
R. Moukhamedov et al., "Use of Polymerase Chain Reaction–Amplified Ribosomal Intergenic Sequence for the Diagnosis of Verticillium Tricorpus," Phytopathology, The American Phytopathological Society, vol. 84, No. 3, 1994, pp. 256–260.

* cited by examiner

*Primary Examiner*—Juliet C. Switzer
(74) *Attorney, Agent, or Firm*—Foley & Lardner LLP

(57) ABSTRACT

This invention relates to *Viola* specific DNA sequences and methods for identification of *Viola* species using the said sequences. The invention also relates to a method for detection of adulteration in 'banafsha' by polymerase chain reaction method. Particularly this invention relates to a very sensitive, accurate and efficient method for identification of *Viola* species from even the powdered form of the plant or its admixtures with other plant species. More particularly, the method is designed to test the genuineness of 'banafsha'.

2 Claims, 4 Drawing Sheets

Figure No:1
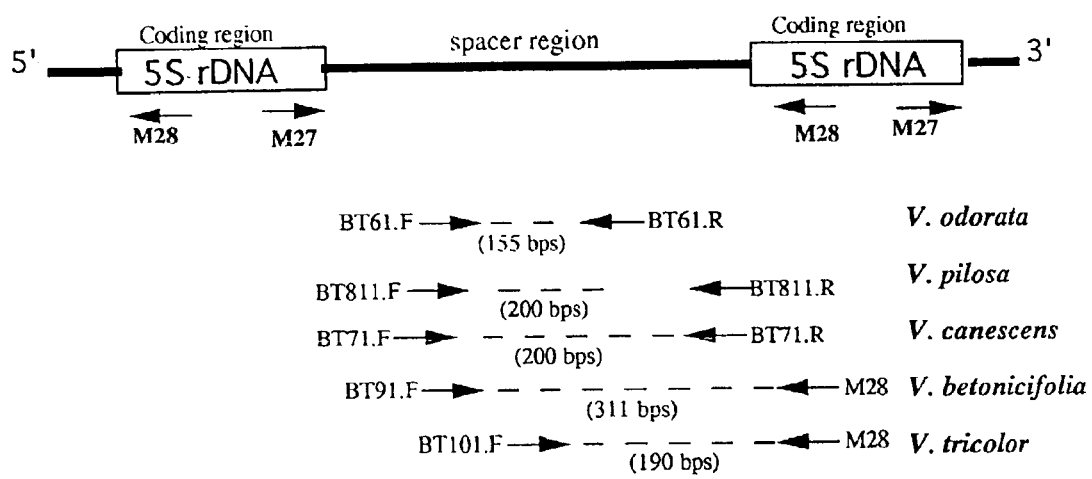

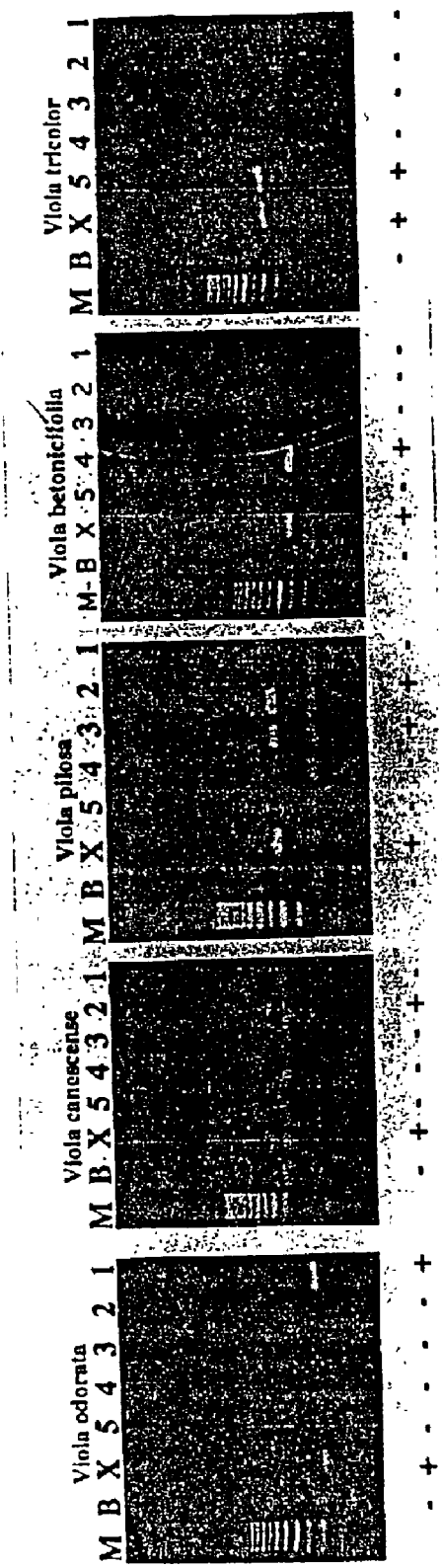
Figure No:2

Figure No:3
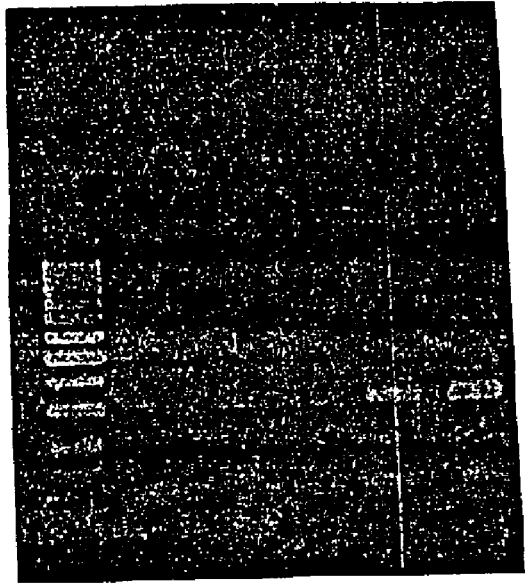
Figure No:4
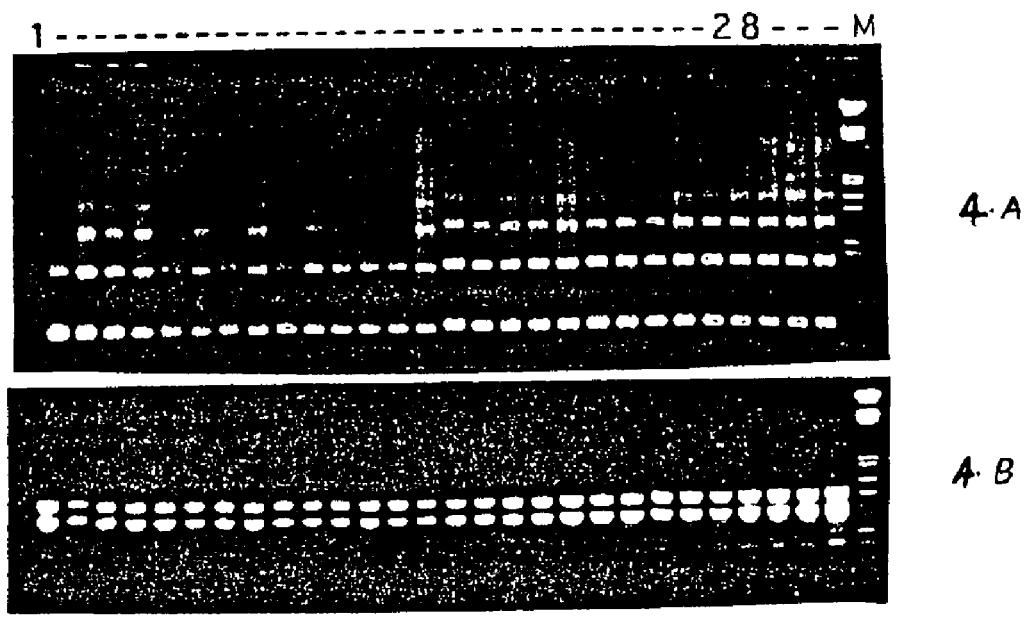

Figure No:5
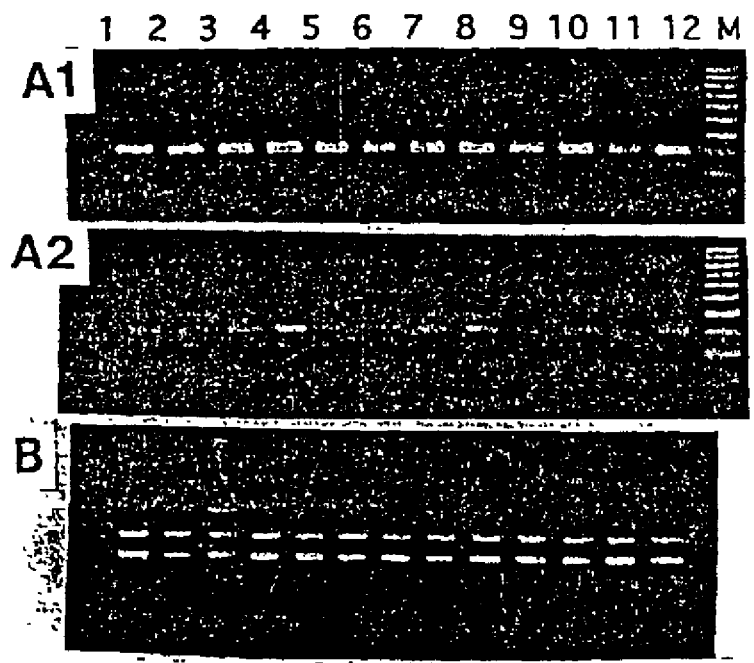
Figure No:6
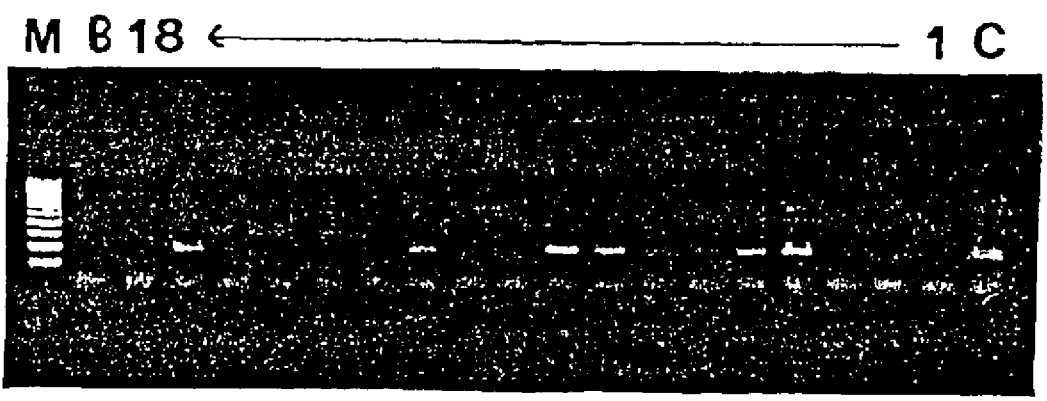

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
ggtgagaact ctcgagggtc ggga                                            24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
gccccgatcc gacacccgag c                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
ccctcactcc tcgagaatat g                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ctatttactt ctctcaccgc g                                               21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 5
tttgtaaaca cggagggggc                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
acaaacccac gattggattg                                              20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 7
ttgtaaacac agaggaggg                                               19

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
cacgattgga ttacacgc                                                18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
tttagtgctg gtatgatcgc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
tgggaagtcc tcgtgttgca                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
taatacgact cactataggg                                              20

<210> SEQ ID NO 12
<211> LENGTH: 24
```

-continued

```
<212> TYPE: DNA
<213> ORGANISM: Artificial Sequence
<220> FEATURE:
<223> OTHER INFORMATION: Description of Artificial Sequence: Primer

<400> SEQUENCE: 12
cgccagggtt ttcccagtca cgac                                           24
```

SPECIES SPECIFIC DNA SEQUENCES AND THEIR UTILIZATION IN IDENTIFICATION OF VIOLA SPECIES AND AUTHENTICATION OF "BANAFSHA" BY POLYMERASE CHAIN REACTION

FIELD OF THE INVENTION

The invention relates to *Viola* specific DNA sequences and methods for identification of *Viola* species using the said sequences. The invention also relates to a method for detection of adulteration in 'banafsha' by polymerase chain reaction method. Particularly this invention relates to a very sensitive, accurate and efficient method for identification of *Viola* species from even the powdered form of the plant or its admixtures with other plant species. More particularly, the method is designed to test the genuineness of 'banafsha'.

BACKGROUND OF THE INVENTION

*Viola* belonging to the family Violaceae is a genus of mostly perennial herbs. They are almost cosmopolitan but mostly distributed in the temperate zones and restricted to the mountains in the tropics (Anonymous, 1965, Indian Pharmacopoeia, $2^{nd}$ Edn. Govt. of India; Anonymous, 1976, Wealth of India, PID, CSIR, New Delhi, Vol. X: 514–517). There are about 400 species of Viola, of which about 30 species are found in India. *Viola* species commonly known as "violets" or "pansies" hybridize freely in nature and, therefore, are difficult to be distinguished taxonomically (Anonymous, 1976, Wealth of India, PID, CSIR, New Delhi, Vol. X: 514–517). The plants are available as different cyto types with 2n=20, 37, 54 etc. in nature (Canne, J. M., 1987, Canad J. Bot., 65; 653–655). Most of the *Viola* species yield perfumes and medicaments, while some are ornamentals (Woodland, D. W., 1991, Contemporary plant systematics, Prentice Hall, Eaglewood, Cliffs). The most important among these species, which is known for its medicinal significance in indigenous system of medicine, is *Viola odorata* L., which is considered to constitute the genuine drug called "Banafsha" (Handa, K. L., Kapoor, L. D., Chopra, I. C. and Nath, S., 1951, Indian J. Pharmacy, 13: 29–48). The whole plant is used in medicine and is available usually in 3 forms: 1) the dried aerial parts of the herb i.e. the stem, leaves and flowers; 2) only dried flowers and 3) aerial parts without flowers. The plant is valued as sedative, expectorant, diaphoretic, antipyretic, diuretic, emetic, purgative, hypotensive and as a laxative (Kirtikar, K. R. and Basu, B. D., 1933, Indian Medicinal Plants, I: 205–212, Lalit Mohan Basu, Allahabad; Chopra, R. N., Nayer, S. L. and Chopra, I. C., 1956, Glossary of Indian Medicinal Plants, CSIR, New Delhi). It has also been reported to be antimycotic and antibacterial and is used for the treatment of eczema and inflammation. The flowers are credited with emollient and demulcent properties and are used as remedy for cough, sore throat, hoarseness, ailments of infants, billiousness and lung troubles and are also listed in French Pharmacopoeia (Lamaison, J. L., Petitjean, C. F. and Carnet, A., 1991, Plantes-Medicinales—et Phytotherapie, 25: 79–88). In Unani system of medicine, this plant is the main ingredient of "Joshanda" consisting of mixtures of drugs and it is mostly used for cold, catarrhal, cough, and associated fevers (Khetrapal, K., Khanna, T., Arora, R. B. and Siddiqui, H. H., 1987, Indian J. Pharmacy, 19: 200–204). The drug is prescribed mainly in the form of decoction, jam or syrup.

In India, *Viola odorata* wildly grows mainly in Jammu and Kashmir and often cultivated elsewhere particularly in West Bengal, Gujarat, Andhra Pradesh, Karnataka and Tamilnadu (Sharma, B. D., Balkrishan, N. P. 1993, Flora of India 2: 351–379). Due to the limited distribution and high demand of *Viola odorata*, which is the main source of banafsha, alternate species including *V. betonicifolia, V. biflora, Viola canescens, V. pilosa, V. sylvestris* and *V. tricolor* (some of which grow abundantly through out the hilly regions of India) have been reported to be supplied in the market as banafsha, either in the pure form or after mixing with *V. odorata* (Handa, K. L., Kapoor, L. D., Chopra, I. C. and Nath, S., 1951, Indian J. Pharmacy, 13: 29–48: Dhar, et al, 1968, Indian J. Exp. Biol., 6: 245; Mehrotra, S., Rawat, A. K. S. and Shome, U., 1998, Natural Plant Sci., 4: 14–22) which have led to the questionable efficacy of the drug, undermining the importance of *Viola* in medicine as originally defined (Kirtikar, K. R. and Basu, B. D., 1933, Indian Medicinal Plants, I; 205–212, Lalit Mohan Basu, Allahabad; Handa, K. L., Kapoor, L. D., Chopra, I. C. and Nath, S., 1951, Indian J. Pharmacy, 13: 29–48). It has also been reported that the roots of *Viola odorata, V. cinerea* and *V. tricolor,* which are emetic in nature, are also used as substitute or adulterants of ipecac drug, which originally comes from dried roots and rhizomes of *Cephaelis ipecacuanha* of family Rubiaceae (Ananymous, 1976, Wealth of India, PID, CSIR, New Delhi, Vol X: 514–517; Chopra, R. N., Nyer, S. L. and Chopra, I. C. Glossary of Indian Medicinal Plants, 1956, Edn. CSIR, New Delhi, 256). It is imperative, therefore, to identify the species composition of banafsha and other herbal medicines before using them in various medicinal preparations, specially by the industrial houses. The classical ways of identifying herbal medicines are based on the morphological, anatomical and chemical analysis using a variety of modern tools (Thankamma, A., Radhika, L. G., 1997, Aryavaidyan, XI: 52–56; Chauhan, S. K., Singh, B. P., Agarwal, S., 1995, Indian Drugs, 36: 189–191; Gawan, S. and Grampurohit, N. D., 1999, Indian Drugs, 36: 175–180). However, the structures and chemical profiles of the medicinal herbs are effected during sample processing and also by environmental and developmental factors during plant growth (Li, P., Pu, Z. M., Jiang, X., Liu, H. J., Xu, G. J., 1994, J. Plant Res. Envir., 3: 60–63; Cai, Z. H., Li, P., Dong, T. T. X. and Tsim, K. W. W., 1999, Planta Medica, 65: 360–364), for example, where market samples are in dry and powdered form, it is difficult to identify plant species by morphological characters. Similarly age, origin, harvesting period and the method of drying of plants may lead to the differences in the secondary product formation and may interfere in identification based on chemical analysis.

Molecular markers are helpful in such situations, since they are independent of environmental and developmental factors. They can be obtained even from dried and powdered herbs. RAPD markers have been used to distinguish 3 different series of *Viola tricolor* (Oh, B. J., Ko, M. K., and Lee, C. H., 1998, Plant Breeding, 117: 295–296), to detect individual component of Chinese medicinal prescription (Cheng, K., Tsay, H., Chen, C. and Chou, T., 1998, Planta Medica, 64: 563–565) and to detect dried roots of 3 Paax species and their adulterants (Shaw, P. C. and But, P. P. H., 1995, Planta Medica, 61: 466–469). However, these markers are of little value specially in freely hybridizing populations including Viola. Conserved sequences in such cases could be ideal. In fact, rRNA genes and their associated spacer length variability has been utilized to differentiate fungal species (Nazar, R. N., Hu, X., Schmidt, J., Culham, D. and Robb, J., 1991, Physiol. and Mol. Plant Pathol., 39: 1–11; Robb, J., Moukhamedov, R., Hu, X., plate, H. and Nazar, R. N., 1993, Physiol. and Mol. Plant Pathol. 43: 423–36; Moukhamedov, R. S., Hu, X., Nazar, R. N. and Robb, J., 1994, Phytopathology, 83: 256–259), to identify plant varieties and species (Martsinkovskaya, A. I., Moukhamedov, R. S. and Abdukarimov, A. A., 1996, Plant Mol. Biol. Reportr. 14: 44–49) and also to detect cereal composition in admixtures (Ko, H. L. and Henry, R. J., 1996, Plant Mol Biol. Reportr, 14: 33–43). Here, the applicants describe cloning and sequencing of the spacer regions between 5S rRNA genes in five Viola species, utilization of the sequence differences to detect the individual *Viola* species by a simple polymerase chain reaction and to utilize this technology for authentication of commercial samples of "banafsha".

OBJECTS OF THE INVENTION

The main object of the invention is to provide *Viola* species specific DNA sequences.

Another object of the invention is to provide method for utilisation of the DNA sequences to identify *Viola* species.

Yet another object is to provide PCR based method for authentication of the composition of 'banafsha'.

Still another object is to provide a method for detection of adulteration of 'banafsha' and 'ipecac' drugs.

DETAILED DESCRIPTION OF THE INVENTION

This invention provides *Viola* specific DNA sequences and methods for identification of *Viola* species using the said sequences. The invention also provides a method for detection of adulteration in 'banafsha' by polymerase chain reaction method. Particularly this invention relates to a very sensitive, accurate and efficient method for identification of *Viola* species from even the powdered form of the plant or its admixtures with other plant species. More particularly, the method is designed to test the genuineness of 'banafsha'.

BRIEF DESCRIPTION OF ACCOMPANYING FIGURES

FIG. 1: Diagrammatic illustration of 5SrRNA gene and their associated spacer regions along with species specific primer combinations: M27 and M28 are forward and reverse consensus 5S rRNA gene primers respectively. BT61.F/BT61.R, BT811.F/BT811R, BT71.F/BT71.R, BT91.F and BT101.F are the specific primers based on the DNA sequence of *V. odorata, V. pilosa, V. canescens, V. betonicifolia* and *V. tricolor* respectively. F and R are forward and reverse primers respectively. The expected amplification product size in (base pairs) using either one consensus and the other *Viola* specific primer or both of the *Viola* specific primers are shown. The 5SrRNA coding region is ~120 bps long.

FIG. 2: Species specific PCR products individually as well as in admixtures: lanes 1 to 5 are *V. odorata, V. canescens, V. pilosa, V. betonicifolia* and *V. tricolor* respectively. Lane X is mixture of all the 5 species DNA. B is blank lane without template DNA and M is mol. wt. marker e.g. 100 bp ladder. + and − shows presence or absence of the amplification product. Sets of primers used for the species shown on top of the gels were as illustrated in FIG. 1.

FIG. 3: PCR product obtained using *V. pilosa* or *V. canescens* specific primers with admixtures of *Viola* species DNA minus *V. pilosa* or *V. canescens:* lanes 1 and 2 are with *V. pilosa* specific primers while lanes 3 and 4 are with *Viola canescens* specific primers. Lanes 1 and 3 were obtained with all DNA templates minus *V. canescens* while lanes 2 and 4 have all DNA templates minus *V. pilosa* DNA. Lane B is blank lane with no DNA and M is mol. wt. marker 100 bp ladder.

FIG. 4: PCR products of 28 individual plants of *Viola pilosa* obtained from 2 independent plots: lanes 1 to 28 represent individual plants. M is mol. wt. marker λ HindIII/EcoRI double digest. Panel A shows PCR products using 5S rRNA gene consensus primers set M27 and M28 while panel B shows RAPD products of same plants using OPE-09 primer.

FIG. 5: Intra-species genetic homogeneity in *Viola betonicifolia:* lanes 1 to 12 represent different plants. M is mol. wt. marker 100 bp ladder. Panel A1 shows PCR products using *V. betonicifolia* specific set of primers. Panel A2 is same PCR product after denaturation. Panel B shows RAPD patterns of the same plants using OPE-09 primer.

FIG. 6: Survey of *Viola canescens* in market samples of banafsha: Panel A shows *V. canescens* specific primers. Lanes 1 to 18 represents samples from various markets of India as listed serially in table 3. C is positive control lane. M is mol. wt. marker 100-bp ladder.

DETAILED DESCRIPTION OF THE INVENTION

Accordingly, the present invention provides species specific DNA sequences and their utilization in identification of *Viola* species and authentication of 'banafsha' by polymerase chain reaction, which comprises: a) unique sequences of 5 *Viola* species, b) unique set of *Viola* species specific PCR primers, c) a PCR based method to identify *Viola* species and d) a PCR based method to detect adulteration of banafsha even in dry powdered form.

In an embodiment of the present invention genomic DNA from 5 different *Viola* species was used (table 1).

TABLE 1

| List of Viola species used in this work. | |
|---|---|
| S. No. | Species name |
| 1. | Viola odorata |
| 2. | Viola pilosa |
| 3. | Viola canescens |
| 4. | Viola betonicfolia |
| 5. | Viola tricolor |

In another embodiment of the present invention genomic DNA from various market samples of banafsha were used (table 2).

TABLE 2

| List of various markets of India from which "banafsha" samples were obtained. | |
|---|---|
| S. No. | Market |
| 1. | Srinagar (J & K) |
| 2. | Jammu (J & K) |
| 3. | Pathankot (Punjab) |
| 4. | Amritsar (Punjab) |
| 5. | Chamba (H.P.) |
| 6. | Shimla (H.P.) |
| 7. | Dharamshala (H.P.) |
| 8. | Jogindernagar (H.P.) |
| 9. | Kullu (H.P.) |
| 10. | Delhi (Khari baori) |
| 11. | Delhi (Karol bagh) |

TABLE 2-continued

List of various markets of India from which "banafsha" samples were obtained.

| S. No. | Market |
|---|---|
| 12. | Lucknow (U.P.) |
| 13. | Dehradun* (U.P.) |
| 14. | Gwalior (Morar) |
| 15. | Hyderabad (A.P.) |
| 16. | Aurangabad$ |
| 17. | Aurangabad$ |
| 18. | Sholapur@ (Maharashtra) |

Note
*Sarnimal bazar;
$Pandariba road;
@East mangaiwar road

In yet another embodiment of the present invention plasmid pMOS Blue T-vector DNA was used.

Genomic DNA extraction: The genomic DNA was isolated using the protocol of Saghai-Maroof et al. (Saghai-Maroof, M. A., Soliman, K. A., Jorgenson, R. A. and Allard, R. W., 1984, Proc. Natl. Acad. Sci. (USA), 81: 8014–18) as modified by us earlier (Singh, M., Sharma, C., and Ahuja, P. S., 1999, Plant Mol Biol Reportr 17: 73).

PCR amplification, subcloning and sequencing of the amplified products: The consensus primers complementary to and based on the sequences of the 3' and 5' ends of the 5S rRNA gene coding regions for plant as described earlier (Kanazin, V., Ananiev, E. and Blake, T., 1993, Genome, 36: 1023–28; Cox, V., Bennett, M. D. and Dyer, T. A., 1992, Theor Appl Genet, 83: 684–90) were got synthesized from "Bangalore Genei (Pvt) Ltd", India. The sequences of these forward and reverse primers were (SEQ ID NO: 9) 5'-TITAGTGCTGGTATGATCGC-3' (M27) and 5'-TGGGAAGTCCTCGTGfITGCA-3' (SEQ ID NO: 10) (M28) respectively. They were used to amplify the non coding spacer regions between 5S rRNA genes. A 25 µl PCR reaction mix contained 2.5 µl of 1 of 10×PCR buffer, 1 µl of dNTPs (stock of 2.5 mM each), 1 µl each of forward and reverse primers (10 pico moles), 1.5 mM $M_gCl_2$ and 0.5 units of Taqpolymerase. The PCR was performed in a Robocycler (Stratagene, La Jolla, Calif.) machine programmed for an initial heating at 94° C. for 3 min and then for 40 cycles at 94° C., 30 sec; 68° C., 30 sec and 72° C., 30 sec. The final extension cycle at 72° C. was kept for 7 more minutes. The PCR products were analyzed in a 1.4% agarose gel and visualized in an ethidium bromide staining under UV light. The lowest densely visible bands in each of the five species were excised from the agarose gels and purified using QIA quick gel extraction Kit (Qiagen). The purified DNA was ligated in the pMOS Blue t-vector overnight at 16° C. as per manufacturers instruction (Amersham Life Sciences). The ligated mixture was transformed into E.Coli MOS Blue cells and selected onto X-Gal, IPTG and ampicillin (100 µg/ml) containing Luria Bertani (LB) agar plates. Ten white colonies identified by colour selection were grown in 5 ml LB liquid medium overnight. The mini preparations of the plasmids were performed using alkaline lysis method (Sambrook, J., Fritsch, E. F. and Maniatis, T., 1989, Molecular cloning: A laboratory manual. $2^{nd}$ Edn., Cold Spring Harbour Laboratory Press, NY). The correct DNA inserts were verified by restriction analysis. Finally one plasmid clone from each plant was selected and its DNA prepared using Qiaquick plasmid DNA isolation Kit (Qiagen) which was then subjected to sequencing in both the directions using the T7 promoter primers (SEQ ID NO: 11) (5'-TAATACGACTCACTATAGGG-3') and M13 forward primer (SEQ ID NO: 12) (5'-CGCCAGGGTTTTCCCAGTCACGAC-3') respectively on an applied Biosystems model 377 automatic DNA sequencing system.

Sequence analysis and species specific primer design: The sequencing data obtained from spacer regions between 5S rRNA genes were analyzed using the PC Gene software. The complementary sequence from spacer regions specific to a particular Viola species which were dissimilar to other species were selected to be used as species specific primers. These primers are listed in table 3. The specific sets of primers used to obtain a species specific PCR product and the sizes of the products are illustrated in FIG. 1.

TABLE 3

Species specific primers used in this study SEQ ID NOS 1–8 respectively, in order of appearance).

| S. No | Primer code | Sequence | Total bases |
|---|---|---|---|
| 1. | BT61.F | 5'---GGTGAGAACTCTCGAGGGTCGGG A---3' | 24 |
| 2. | BT61.R | 5'---GCCCCGATCCGACACCCGAGC---3' | 21 |
| 3. | BT101.F | 5'---CCCTCACTCCTCGAGAATATG---3' | 21 |
| 4. | BT91.F | 5'---CTATTTACTTCTCTCACCGCG---3' | 21 |
| 5. | BT811.F | 5'---TTTGTAAACACGGAGGGGGC---3' | 20 |
| 6. | BT811.R | 5'---ACAAACCCACGATTGGATTG---3' | 20 |
| 7. | BT71.F | 5'---TTGTAAACACAGAGGAGGG---3' | 19 |
| 8. | BT71.R | 5'---CACGATTGGATTACACGC---3' | 18 |

In an embodiment BT 61.F and BT 61.R sequences when used as a primer, provides a single band as PCR product of 150 bps in the species Viola odorata.

In another embodiment BT 71.F and BT 71.R sequences when used as a primer, provides a single band as PCR product of 200 bps in the species Viola canescens.

In still another embodiment BT 811.F and BT 811.R sequences when used as a primer, provides a single band as PCR product of 200 bps in the species Viola pilosa.

In yet another embodiment BT 91F and M-28 sequences when used as a primer, provides a single band as PCR product of 311 bps in the species Viola betonicifolia.

In an embodiment BT 101.F and M-28 sequences when used as a primer, provides a single band as PCR product of 190 bps in the species Viola tricolor.

In an embodiment the sequences specific to Viola species at an optimized PCR annealing temperatures of 68° C. for V. odorata, 62° C. for V. canescens, 62° C. for V. pilosa, 52° C. for V.botonicifolia and 52° C. for V. tricolor.

In an embodiment, the sequences specific to Viola species at an optimized PCR annealing time, said time being 15 second for V. odorata, 24 second for V. canescens, 22 second for V. pilosa and 30 second for V. betonicifolia and V. tricolor respectively.

In yet another embodiment, the sequences specific to Viola species at an optimized PCR extension time of 18 second for V. odorata, 17 second for V. canescens, V. pilosa, V. betonicifolia and V. tricolor respectively.

In yet another embodiment the sequences specific to Viola species at an optimized concentration of $MgCl_2$ ions of 0.85 mM for *V. odorata,* 1.5 mM for *V. canescens,* 1.1 mM for *V. pilosa,* 0.55 mM for *V. betonicifolia* and 0.45 mM for *V. tricolor* respectively.

In yet another embodiment the sequences specific to *Viola* species at an optimized primer concentration of 8–10 picomoles.

In yet another embodiment the sequences specific to *Viola* species give the same PCR product with DNA isolated from *Viola* different plant parts i.e. from roots, rhizome and flowers.

The following examples are given by way of illustration of the present invention and should not be construed to limit the scope of the present invention.

EXAMPLE 1

Majority of the *Viola* Species Specific Primers Amplify Only Corresponding Species:

PCR amplification products using a set of primers, either one of the species specific and the other consensus or both species specific primers (as illustrated in FIG. 1) were obtained for all five species. The PCR reaction contained 2.5 μl of 10×PCR buffer, 1 μl of dNTPs (mix of 2.5 mM each), 2–10 ng DNA, 8–10 picomole of each primer, 0.5 units of Taq polymerase and a variable concentration (0.45–1.5 mM depending upon the *Viola* species as shown in table 4) of $MgCl_2$ in a 25 μl reaction mix. The DNA was denatured at 94° C. for 3' and then subjected to PCR upto 40 cycles. A last extension cycle of 2 min in each case was also given at 72° C. The annealing and extension temperatures and the times along with $MgCl_2$ concentration were optimized for each of 5 *Viola* species with each set of primers (table 4) and are discussed below:

*Viola odorata:* Using 8 picomole each of the forward and reverse primers (BT61.F and BT61.R) respectively along with annealing at 68° C. for 15 sec, extension time of 18 seconds and a concentration of 0.85 mM of $MgCl_2$ was optimized to give a band of 150 bps as expected with only *V. odorata* but not with any of the other plants (FIG. 2, panel A, lane 1). There was also a similar amplification product when the genomic DNA of all the five plant species were mixed in equal ratio (FIG. 2, panel A, lane X). The PCR product was *V. odorata* genome specific and could be detected reproducibly in mixture of all the 5 plant species. There was no significant difference in the band intensity when the genomic DNA from fresh tissues or the dried tissues were taken. Increasing $MgCl_2$ concentration or the annealing time led to the appearance of a few faint bands of high molecular weight.

*Viola canescens:* Use of BT71.F and BT71.R as forward and reverse primers respectively along with an annealing temperature of 62° C. for 24 sec and an extension time of 17 sec along with a $MgCl_2$ concentration of 1.5 mM gave an expected band of 200 bps with only *V. canescens* as well as in the mixed samples of all 5 *Viola* species but not individually with any of the other 4 DNA templates (FIG. 2, panel B, lanes 2 and X respectively). Increasing annealing temperature beyond 62° C. led to no amplification while reducing temperature led to appearance of several faint bands in addition to 1 prominent expected band.

*Viola pilosa:* Similarly use of BT811.F and BT811.R set of primers along with cycling parameters of annealing at 62° C. for 22 sec and extension for 17 sec along with a $MgCl_2$ concentration of 1.1 mM gave a band of expected size of 200 bps with *V. pilosa* and *V. canescens* but not with any of the other plants tested (FIG. 2, panel C, lanes 2 and 3). Similar amplification product was obtained when the genomic DNA of all the five plant species were mixed in equal ratio (lane X). To demonstrate that *V. pilosa* specific primers detect both *V. pilosa* and *V. canescens* but *V. canescens* specific primers detect only *V. canescens* specifically, the applicants used species specific primers for these species to amplify mixtures of 4 *Viola* species DNA templates minus *V. pilosa* or *V. canescens*. As shown in FIG. 3 *V. pilosa* specific primers detect both *V. pilosa* and *V. canescens* but not vice versa.

*Viola betonicifolia:* Using BT91.F and M28 as forward and reverse primers respectively along with an annealing temperature of 52° C. for 30 sec, an extension time of 17 sec, and $MgCl_2$ concentration of 0.55 mM gave an expected band of 311 bps with only *V. betonicifolia* or in a mixture of all 5 species but not with any of the other plants individually (FIG. 2, panel D, lanes 4 and X respectively).

*Viola tricolor:* Using BT101.F and M28 set of primers along with an annealing temperature of 52° C. for 30 sec, an extension time of 17 sec, along with a $MgCl_2$ concentration of 0.45 mM gave an expected band of 190 bps with only *V. tricolor* or in a mixture of all 5 species but not with any of the other plants (FIG. 2, panel E, lanes 5 and X respectively). Surprisingly *V. tricolor* and *V. betonicifolia* required almost similar amplification conditions (Table 4).

TABLE 4

Standardized parameters for PCR amplification.

| S.N. | Parameter | V.O. | V.P. | V.C. | V.B. | V.T. |
|---|---|---|---|---|---|---|
| 1. | $MgCl_2$ (mM) | 0.85 | 1.1 | 1.5 | 0.55 | 0.45 |
| 2. | Annealing | | | | | |
| | Temp (° C.) | 68 | 62 | 62 | 52 | 52 |
| | Time (sec) | 15 | 22 | 24 | 30 | 30 |
| 3. | Extension time (sec) | 18 | 17 | 17 | 17 | 17 |

EXAMPLE 2

Conserved 5S rRNA Gene Based Primers (3' and 5') Gave an Identical Amplification Product in 28 Individual Plants of *Viola pilosa:*

In order to find out 5S rRNA associated spacer length and sequence variability within the individuals of a species, the applicants analyzed 28 individuals plants of *V. pilosa* selected randomly from 2 plots (from IHBT campus, Palampur and Jogindernagar Herbal Garden, Jogindernagar), for their amplification products using consensus 5S rRNA primers M27 and M28. As shown in FIG. 4A, all the plants gave identical banding patterns. When these plants were subjected to RAPD analysis using OPE-09 primer they again showed identical banding patterns (FIG. 4, panel B). When 2 more primers were analyzed they showed some differences in many of the plants as expected ( data not shown).

EXAMPLE 3

*Viola betonicifolia* Specific Primers Gave an Identical Amplification Product in 12 Individual Plants Collected from Nature:

Similar to example 1, 12 individual plants of *V. betonicifolia* were analyzed for their amplification products using *V. betonicifolia* species specific set of primers (BT91.F and M28 as illustrated in FIG. 2). As shown in FIG. 5A1, all the plants gave identical banding patterns. These PCR products when denatured and analyzed in a 1.8% agarose gel again revealed identical banding patters (FIG. 5, panel A2). When these plants were subjected to RAPD analysis using OPE-09 primers they showed little differences, for example, in lane no 2 and 3 the $3^{rd}$ band from top is present only in 4 samples which is different in size in lane number 8 (FIG. 5, panel B).

EXAMPLE 4

Market Samples of Banafsha Revealed that Majority of Them Were Fake Samples:

In order to find but the genuineness of banafsha, the applicants analyzed 18 market samples of banafsha collected from different markets during 1997–99 for their amplification products using *V. canescens* specific primers. FIG. 6 shows that 7 samples were positive for *V. canescens* which does not represent genuine banafsha. This example clearly demonstrate that the developed PCR band approach works well for market samples.

The main advantages of the present invention are:
1. It is specific to *Viola odorata, V. pilosa, V. canescens, V. betonicifolia* and *V. tricolor*.
2. It is highly sensitive and only nanogram amounts of DNA is required.
3. It can work equally well for degraded DNA.
4. Only mg amounts of samples are required.
5. It can work well for the processed and powdered samples.
6. It can detect presence of *Viola* species even in admixtures of samples and herbal formulations.
7. The presence of *Viola* species specific PCR products can be visualized in a simple agarose gel and no hazardous radioactive labeling or time consuming and complex systems are needed.
8. It is rapid.
9. It has a potential for automation.

What is claimed is:

1. A method of detecting adulteration in samples of herb *Viola odorata* by other *Viola* species, said method comprising steps of:
   a. amplifying the sample DNA by PCR using a pair of primers selected from the group consisting of the following primer parts BT 71.F (SEQ ID NO: 7) and BT71.R (SEQ ID NO: 8); BT 811.F (SEQ ID NO: 5) and BT811.R (SEQ ID NO: 6); BT 91.F (SEQ ID NO: 4) and M-28 (SEQ ID NO: 10); and BT 101.F (SEQ ID NO: 3) and M-28 (SEQ ID NO: 10); and
   b. detecting the adulterated sample as the amplified sample.

2. A method as claimed in claim 1, wherein the method is used to identify genuine Banafsha.

* * * * *